US006548481B1

(12) United States Patent
Demuth et al.

(10) Patent No.: US 6,548,481 B1
(45) Date of Patent: Apr. 15, 2003

(54) EFFECTORS OF DIPEPTIDYL PEPTIDASE IV

(75) Inventors: Hans-Ulrich Demuth, Halle/Saale (DE); Konrad Glund, Halle/Saale (DE); Dagmar Schlenzig, Halle/Saale (DE); Susanne Kruber, Halle/Saale (DE)

(73) Assignee: Probiodrug AG, Halle/Salle (DE)

( * ) Notice: Subject to any disclaimer, the term of this patent is extended or adjusted under 35 U.S.C. 154(b) by 0 days.

(21) Appl. No.: 09/723,638

(22) Filed: Nov. 28, 2000

Related U.S. Application Data

(63) Continuation of application No. PCT/EP99/03712, filed on May 28, 1999.

(30) Foreign Application Priority Data

May 28, 1998 (DE) ........................................ 198 23 831

(51) Int. Cl.$^7$ ........................ A61K 38/05; A61K 38/48; A61K 31/44
(52) U.S. Cl. ............................. 514/19; 514/2; 514/183; 424/94.63; 424/94.64; 548/200; 544/141; 544/333
(58) Field of Search .................. 514/2, 19, 183; 548/200; 544/141, 333; 424/94.63, 94.64, 185.1

(56) References Cited

U.S. PATENT DOCUMENTS

| | | | |
|---|---|---|---|
| 2,961,377 A | 11/1960 | Shapiro et al. ................. | 167/65 |
| 3,174,901 A | 3/1965 | Sterne .......................... | 167/65 |
| 3,879,541 A | 4/1975 | Kabbe et al. ................. | 424/326 |
| 3,960,949 A | 6/1976 | Ahrens et al. ............. | 260/564 B |
| 4,028,402 A | 6/1977 | Fischer et al. .......... | 260/501.14 |
| 4,935,493 A | 6/1990 | Bachovchin et al. ........ | 530/331 |
| 5,433,955 A | 7/1995 | Bredehorst et al. ......... | 424/94.3 |
| 5,462,928 A | 10/1995 | Bachovchin et al. .......... | 514/19 |
| 5,512,549 A | 4/1996 | Chen et al. .................... | 514/12 |
| 5,543,396 A | 8/1996 | Powers et al. ................ | 514/19 |
| 5,614,379 A | 3/1997 | Mackellar ................... | 435/68.1 |
| 5,624,894 A | 4/1997 | Bodor ........................... | 514/2 |
| 5,939,560 A | 8/1999 | Jenkins et al. .............. | 548/535 |
| 6,006,753 A | 12/1999 | Efendic ....................... | 128/898 |
| 6,303,661 B1 * | 10/2001 | Demuth et al. ............. | 514/866 |

FOREIGN PATENT DOCUMENTS

| | | | | |
|---|---|---|---|---|
| JP | 04-288098 | 10/1992 | ............ | C07K/7/06 |
| JP | 4334357 | 11/1992 | | |
| WO | WO 91/11457 | 8/1991 | ............ | C07K/7/34 |
| WO | WO 91/16339 | 10/1991 | ............ | C07K/5/10 |
| WO | WO 91/17767 | 11/1991 | .......... | A61K/37/54 |
| WO | WO 93/08259 A2 | 4/1993 | | |
| WO | WO 95/11689 | 5/1995 | .......... | A61K/37/00 |
| WO | 9515309 | 6/1995 | | |
| WO | WO 95/29691 | 11/1995 | .......... | A61K/31/675 |
| WO | 9740832 | 11/1997 | | |
| WO | WO 97/45117 | 12/1997 | .......... | A61K/31/435 |
| WO | WO 98/19998 | 5/1998 | .......... | C07D/207/00 |
| WO | WO 98/22494 | 5/1998 | ............ | C07K/5/00 |
| WO | WO 00/01849 | 1/2000 | ............ | C12Q/1/68 |
| WO | WO 00/53171 | 9/2000 | .......... | A61K/31/155 |
| WO | WO 01/62266 A2 | 8/2001 | .......... | A61K/38/00 |

OTHER PUBLICATIONS

Chemical Abstracts, vol. 115. No. 15, 14. Oktober 1991 (Oct. 14, 1991) Columbus, Ohio, US; abstract No. 149947q, Schoen Ekkehard et al: "Dipeptidyl peptidase IV in the immune system.Effects of specific enzyme inhibitors on activity of dipeptidyl peptidase IV and proliferation of human lymphocytes" Seite 37; XP002114197 Zusammenfassung & Biol. Chem. Hoppe–Seyler, Bd. 372, Nr. 5, 1991, Seiten 305–311.

Database WPI, Section Ch, Week 9217, Derwent Publications Ltd., London, GB; AN 92–132891, XP002041622 & DD 296 075 A (Luther–Univ. Halle), Nov. 21, 1991 in der Anmeldung erwähnt Zusammenfassung.

Chemical Abstracts, vol. 126, No. 2, 13.Januar 1997 (Jan. 13, 1997) Columbus, Ohio, US; abstract No. 16161j, Stoeckel A. et al: "Competitive inhibition of proline specific enzymes by amino acid thioxopyrrolidides and thiazolidides" Seite 241; XP002114198 Zusammenfassung & Pept: Chem., Struct.Biol., Proc.Am.Pept.Symp., Nr. 14, 1995, Seiten 709–710.

Chemical Abstracts, vol. 118, No. 25, 21. Juni 1993 (Jun. 21, 1993) Columbus, Ohio, US; abstract No. 255342k, Seite 933; CP002114199 Zusammenfassung & JP 04 334357 A (Fujerebio Inc) Nov. 20, 1992.

Heihachiro et al: "Synthesis of prolyl endopeptidase inhibitors and evaluation of their structure–activity relationships : in vitro inhibition of prolyl endopeptidase" Chemical and Pharmaceutical Bulletin., Bd. 41, Nr. 9, 1993, Seiten 1583–1588, XP002114196 Pharmaceutical Society of Japan, Tokyo., JP ISSN: 0009–2363 das ganze Dokument.

Merck Index, 11$^{th}$ Edition, p. 934.

J. Lin et al.: "Inhibition of depeptidyl peptidase IV by fluoroolefin–containing n–peptidyl–0–hydroxylamine peptidomimetics" Proceedigns of the National Academy of Sciences of USA, vol. 95, Nov. 1998.

(List continued on next page.)

Primary Examiner—Karen Cochrane Carlson
Assistant Examiner—Chih-Min Kam
(74) Attorney, Agent, or Firm—John C. Serio, Esq.; Brown Rudnick Berlack Israels LLP

(57) ABSTRACT

Dipeptide compounds and compounds analogous to dipeptide compounds that are formed from an amino acid and a thiazolidine or pyrrolidine group, and salts thereof used in the treatment of impaired glucose tolerance, glycosuria, hyperlipidaemia, metabolic acidoses, diabetes mellitus, diabetic neuropathy and nephropathy and also of sequelae of diabetes mellitus in mammals.

14 Claims, 2 Drawing Sheets

OTHER PUBLICATIONS

Korom, S. et al., Inhibition of CD26/dipeptidyl peptidase IV activity in vivo prolongs cardiac allograft survival in rat recipients, Transplantation vol. 63, p. 1495–1500, Nov. 10, 1997.

Tanaka, S. et al., Suppression of arthritis by the inhibitors of dipeptidyl peptidase IV. Int. J. Immunopharmacol. vol. 19, No. 1, p. 15–24 (1997).

Mentlein, R. et al, proteolytic processing of neuropeptide Y and peptide YY by dipeptidyl peptidase IV. Regul. Pept. 49, 133 (1993).

Wetzl, W. et al., Effects of the CLIP fragment ACTH 20–24 on the duration of REM sleep episodes. Neuropeptides, 31, (1), p. 41–45 (1997).

Amasheh, S. et al., Electrophysiological analysis of the function of the mammalian renal peptide transporter expressed in *Xenopus Laevis oocytes*. J. Physiol. 504, 169–174 (1997).

Wakselman, M. et al., Inhibition of HIV–1 infection of CD 26+ but not CD26–cells by a potent cyclopeptidic inhibitor of the DPP IV activity of CD 26. Abstract P 44 of the 24th European Peptide Symposium 1996.

Thorens, B et al., Glucagon–Like Peptide–I and the Control of Insulin Secretion in the Normal State and in NIDDM. *Diabetes* 42:1219–1225 (1993).

Orskov C. et al., Proglucagon Products in Plasma of Non-insulin–dependent Diabetics and Nondiabetic Controls in the Fasting State and After Oral Glucose and Intravenous Argine. *J. Clin. Invest.* 87:415–423 (1991).

Pauly, R. et al., Improved Glucagon Tolerance in Rats Treated with the Dipeptidyl Peptidase IV (CD26) Inhibitor ILE–Thaxolidide. *Metabolism* 48:385–389 (1999).

Gutniak, M. K. et al., Subcutaneous Injection of the Incretin Hormone Glucagon–Like Peptide 1 Abolishes Postprandial Glycemia in NIDDM. *Diabetes Care* 17:1039–1044, (Sep. 1994).

Willms, B. et al., Gastric Emptying, Glucose Response, and Insulin Secretion after a Liquid Test Meal: Effects of Exogenous Glucagon–Like Peptide–1 (GLP–1–(7–36) Amide in Type 2 (Noninsulin –Dependent) Diabetic Patients. *JCEM* 81:327332 (1996) No. 1 327–332.

Hendrick, G.K. et al., Glucagon–Like Peptide–I–(7–37) Suppresses Hyperglycemia in Rats. *Metabolism* vol. 42, No. 1, p. 1–6 (Jan. 1993).

Deacon, C. et al., Degradation of Glucagon–Like Peptide–1 by Human Plasma in Vitro an N–Terminally Truncated Peptide that is a Major Endogenous Metabolite in Vivo. *JCEM* 80:952–957, (Apr. 25, 1995).

Hoffman, T. et al., Inhibition of Dipeptidyl Peptidase IV (DPIV) by anti–DP IV antibodies and non–substrate X–X–Pro– Oligopeptides Ascertained by Capillary Electrophoresis. *Journal of Chromatography A, 716* 355–362 (1995).

Nauck, M.A. et al., Normalization of Fasting Hyperglycaemia by Exogenous Glucagon–Like Peptide I (7–36 Amide) in Type 2 (Non–insulin–dependent) Diabetic Patients. *Diabetologia* 36:741–744 (1993).

The Merck Index, 12$^{th}$ Edition, An Encyclopedia of Chemicals, Drugs, and Biologicals, 1996, p. 1014.

Martindale The Extra Pharmacopoeia, 30$^{th}$ Edition, London Pharmaceutical Press, 1993, p. 36.

Arai et al: "Synthesis of prolyl endopeptidase inhibitors and evaluation of their structure–activity realtionships : in vitro inhibition of prolyl endopeptidase from Canine Brain" Chemical and Pharmaceutical Bulletin., Bd. 41, No. 9, 1993, pp. 1583–1588.

Durinx, C.; et al.; "Reference Values for Plasma Dipepidyl–Pepidase IV activity and their Association with Other Laboratory Parameters". Clin Chem Lab Med 2001, Feb.; 39 (2) :155–9, 1 page.

Gossrau, R.; "Cytochemistry of Membrane Proteases". Histochem J, Jul.1985,; 17 (7) :737–71, 1 page.

Hahn, T.; et al.; "Enzyme Histochemical Evidence for the Presence of Potential Blood Pressure Regulating Proteases in Cultured Villous Explants from Human First Trimester Placentae". Acta Histochem 1993, Dec., 1995 (2) :185–92, 1 page.

Heymann, E.; et al.; "Has Dipeptidyl Peptidase IV an Effects on Blood Pressure and Coagulation." Klin Wochenschr, Jan. 1984, 2;62 (1) :2–10, 1 page.

Magyar, C.E.; et al.; "Proximal Tubule Na Transporter Responses are the same during Acute and Chronic Hypertension." Am J Physiol Renal Physiol, Aug. 2000,; 279 (2) :F358–69, 1 page.

Papies, B.; et al.; "Isoenzyme (Lactate Dehydrogenase, Aspartate Aminotransferase) and Dipeptidyl Peptidase IV Activity Changes in Blood Plasma Likely Indicative of Organ Involvement due to Arterial Hypertension." Cor Vasa, 1991; 33 (3) :218–26, 1 page.

Qureshi. N.U.; et al., "Endogenous Neuropeptide Y Mediates Vasoconstriction during Endotoxic and Hemorrhagic Shock". Regul Pept, Sep. 1998, 25; 75–76:215–20, 1 page.

Index Nominum, International Drug Directory 1992/1993, Medpharm Scientific Publishers, pp. 728–729.

The Merck Index, An Encyclopedia of Chemicals and Drugs, 9$^{th}$ Edition, Merck & Co., Inc., 1976, p. 773.

C.J. Bailey et al., *New Antidiabetic Drugs*, Smith–Gordon Nishimura, 1990, p. 36.

C.B. Welch, *Medical Management of Non–Insulin–Dependent (Type II) Diabetes*, 3$^{rd}$ edition, American Diabetes Association, "Diagnosis and Classification" p. 3, 1994, Pharmacologic Intervention (1 page).

Mannucci et al., *diabetes Care*, "Effect of Metformin on Glucagon–Like Peptide 1 (GLP–1) and Leptin Levels in Obese Nondiabetic Subjects", 24(3): 489–494, Mar. 2001.

Stryer, *Biochemistry 3$^{rd}$ Ed.*, "Protein Conformation, Dynamics, and Function", 1988, p 191–193.

Pauly et al., *Regulatory Peptides*, "Abstracts Issue: Abstracts form the 11$^{th}$ International Symposium on Regulatory Peptides", Jul. 15, 1996, 64(1–3): 148 plus cover.

Gutniak et al., *New England Journal of Medicine*, "Antidiabetogenic Effect of Glucagon–like peptide–1 (7–36) Amide in Normal Subjects and Patients With Diabetes Mellitus", 1992, 326: 1316–1322.

H.A. Smith et al., *Veterinary Pathology* (fourth edition), "Diseases and Disorders of Metabolism: Deficiency Diseases", 1972, p 1018–1020.

G.G. Duncan, *Diseases of Metabolism (Asian edition)*, "Diabetes Mellitus", 1966, p 951–957.

T.J. Kieffer et al., "Degradation of Glucose–Dependent Insulinotropic Polypetide and Truncated Glucagon–Like Peptide 1 In Vitro and In Vivo by DP IV", Endocrinology, vol. 136(8), 1995, p 3585–3596.

C.F. Deacon et al., *Diabetes*, "Both Subcutaneously and Intravenously Administered Glucagon–Like Peptide I Are Rapidly Degraded from the $NH_2$–Terminus in Type II Diabetic Patients and in Healthy Subjects", Sep. 1995, 44: 1126–1131.

*Vidal*, 1993, 69th Edition, p. 612–613.

*Goodman & Gilman's The Pharmacological Basis of Therapeutics*, Ninth Edition, 1996, p. 1510.

Nathan et al., *Diabetes Care*, "Insulinotropic Action of Glucagonlike Peptide–1–(7–37) in Diabetic and Nondiabetic Subjects", Feb. 1992, 15(2): 270–275.

Frohman et al., *Journal of Clin. Invest.*, "Rapid Enzymatic Degradation of Growth Hormone–releasing Hormone by Plasma in Vitro and in Vivo to a Biologically Inactive Product Cleaved at the $NH_2$ Terminus", vol. 78, Oct. 1986, p 906–913.

Snow et al., *Advances In Medicinal Chemistry*, "Boronic Acid Inhibitors of Dipeptidyl Peptidase IV: A New Class of Immunosuppressive Agents", vol. 3, 1995, p 149–177.

Ashworth et al., *Bioorg. Med. Chem. Lett.*, "2–Cyanopyrrolidides as Potent, Stable Inhibitors of Dipeptidyl Peptidase IV", 1996, 6(10): 1163–1166.

Endroczi et al., *Acta Physiol. Hung.*, "Dipeptidyl peptidase IV (DP IV) and Superoxide Dismutase Activity in Thymus–Derived Lymphocytes: Effects of Inhibitory Pepdides and $Zn^{2+}$ in Vitro", 1990, 75(1): 35–44.

Lee, H.S. et al., "Cathepsin B Inhibitory Peptides Derived from β–Casein," Peptides 21 (2000) 807–809.

Edwards, J.V. et al., *J. Peptide Res.*, "Synthesis and Activity of $NH_2$ –and COOH–Terminal Elastase Recognition Sequences oin Cotton," 1999, 54: 536–543.

* cited by examiner

EFFECTORS OF DIPEPTIDYL PEPTIDASE IV

The present application is a continuation of PCT EP 99/03712 application filed on May 28, 1999 which claim the priority of DE 198/23831.2 filed in May 28, 1998.

BACKGROUND OF THE INVENTION

According to the current state of the art, hyperglycaemia and associated causes and sequelae (including diabetes mellitus) are treated by the administration of insulin (e.g. material isolated from bovine pancreas or obtained by genetic engineering techniques) to the diseased organisms in various forms of administration. All methods known hitherto, including more modern procedures, are distinguished by the requirement of a large amount of material, by high costs and often by a distinct impairment of the quality of life of the patients. The conventional method (daily i.v. insulin injection, customary since the 1930s) treats the acute symptoms of the disease, but after prolonged use leads inter alia to serious vascular changes (arteriosclerosis) and nerve damage.

More recently the installation of subcutaneous depot implants (the insulin is released in metered amounts, and daily injections are unnecessary) and implantation (transplantation) of intact Langerhan's cells into the functionally impaired pancreatic gland or into other organs and tissues have been proposed. Such transplants require a high level of technical resources. Furthermore, they involve a surgical intervention into the recipient organism, which is associated with risks, and even in the case of cell transplants require methods of suppressing or circumventing the immune system.

The use of alanyl pyrrolidide and isoleucyl thiazolidide as inhibitors of DP IV or of DP IV-analogous enzyme activity is already known from PCT/DE 97/00820 and the use of isoleucyl pyrrolidide and isoleucyl thiazolidide hydrochloride is already known from DD 296 075. Isoleucyl thiazolidide, which is used in the latter prior art, is a natural, that is to say L-threo-isoleucyl thiazolidide: on the priority date and also on the application date of the two specifications, only that form, the natural form, of isoleucyl thiazolidide was available.

It has been established that those compounds, especially L-threo-isoleucyl thiazolidide, are good effectors for DP IV and DP IV-analogous enzyme activities, but the use of that compound may give rise to certain problems in the case of some patients or some forms of the disease:

Depending upon the symptoms and the severity e.g. of diabetes mellitus it would be desirable, for example, to have available effectors that have an action different from that of the known compounds: for example, it is known that diabetes mellitus patients must be "stabilised" individually in order that their illness can be treated in an optimum manner. In some cases, for example, a reduction in the activity by DP IV effectors ought to be sufficient. It is also possible that too high a level of inhibitor activity and the permanent administration of the same medicament, especially in view of the life-long duration of treatment, may result in undesirable side-effects. Furthermore, it could also be desirable to improve certain transport properties in order to increase the rate of absorption of the effectors in vivo

SUMMARY OF THE INVENTION

The present invention relates to dipeptide compounds and compounds analogous to dipeptide compounds that are formed from an amino acid and a thiazolidine or pyrrolidine group, and salts thereof, referred to hereinafter as dipeptide compounds, and to the use of the compounds in the treatment of impaired glucose tolerance, glycosuria, hyperlipidaemia, metabolic acidoses, diabetes mellitus, diabetic neuropathy and nephropathy and also of sequelae of diabetes mellitus in mammals.

The invention therefore relates also to a simple method of lowering the blood sugar concentration in mammals with the aid of dipeptide compounds as activity-reducing effectors (substrates, pseudosubstrates, inhibitors, binding proteins, antibodies etc.) for enzymes having activity comparable to or identical to the enzymatic activity of the enzyme dipeptidyl peptidase IV.

DP IV or DP IV-analogous activity (for example the cytosolic DP II has a substrate specificity almost identical to DP IV) occurs in the blood circulation where it splits off dipeptides highly specifically from the N-terminus of biologically active peptides when proline or alanine are the adjacent residues of the N-terminal amino acid in their sequence.

The glucose-dependent insulinotropic polypeptides: gastric inhibitory polypeptide 1-2 ($GIPI_{1-42}$) and glucagonlike peptide amide-1 7-36 ($GLP-1_{7-36}$), that is to say hormones that stimulate glucose-induced secretion of insulin by the pancreas (also called incretins), are substrates of DP IV, since the latter is able to split off the dipeptides tyrosinylalanine and histidylalanine, respectively, from the N-terminal sequences of those peptides in vitro and in vivo.

The reduction of such DP IV and DP IV-analogous enzyme activity of the cleavage of those substrates in vivo can be used to bring about effective suppression of undesired enzyme activity under laboratory conditions and also in the case of pathological conditions in mammalian organisms. For example, diabetes mellitus Type II (including adult-onset diabetes) is based on a reduced secretion of insulin or disorders in the receptor function resulting inter alia from anomalous incretin concentrations arising from proteolysis.

The aim of the invention is therefore to provide new (especially activity-reducing) effectors for the treatment of e.g. impaired glucose tolerance, glycosuria, hyperlipidaemia, metabolic acidoses, diabetes mellitus, diabetic neuropathy and nephropathy and also of sequelae of diabetes mellitus in mammals, and a simple method of treating such diseases.

This aim is achieved according to the invention by the provision of dipeptide compounds or analogues of dipeptides that are formed from an amino acid and a thiazolidine or pyrrolidine group, and salts thereof.

DETAILED DESCRIPTION OF THE INVENTION

Figure 1:
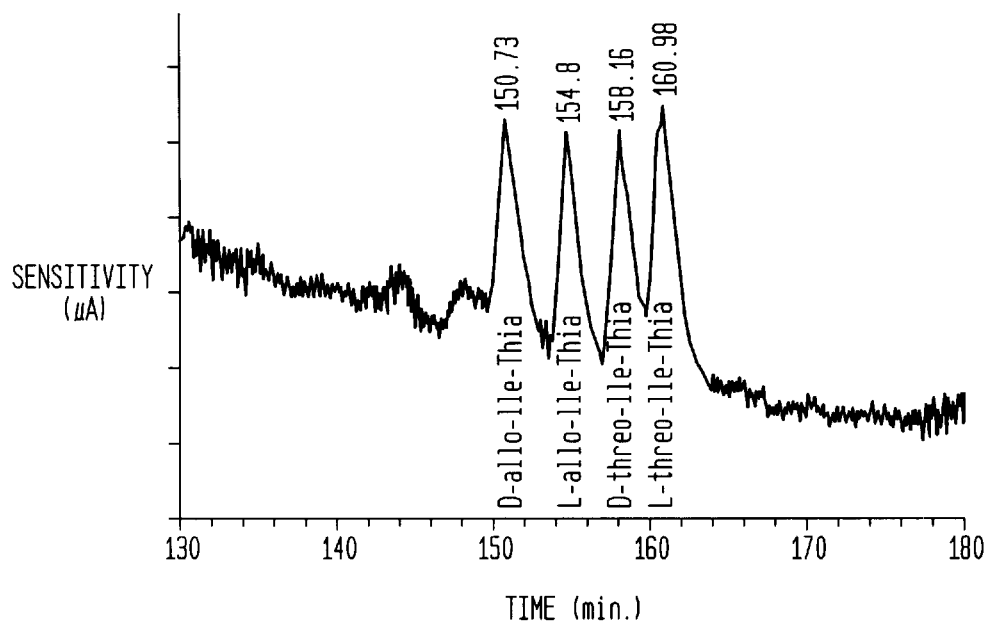
FIG. 1 depicts capillary zone electrophoretic separation of the isomers of isoleucyl thiazolide this separation is representative of a 1:1:1:1 mixture of L-threo-Ile-Thi*fum, L-allo-lle-Thia*fum, D-threo-Ile-Thia* fum, D-allo-Ile-Thia*fum.
Figure 2:
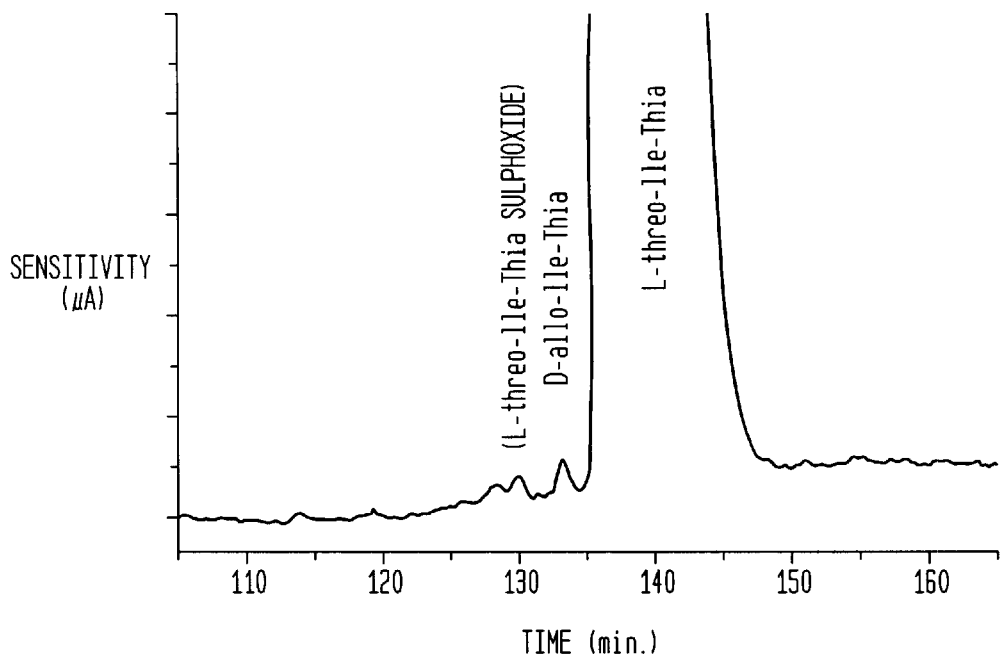
FIG. 2 depicts capillary zone electrophoretic separation of Ile-Thia*fumarate this separation is representative of a 1:1000 mixture of L-threo-Ile-Thia*fumarate to D-allo-Ile-Thia*fumarate.
Figure 3:
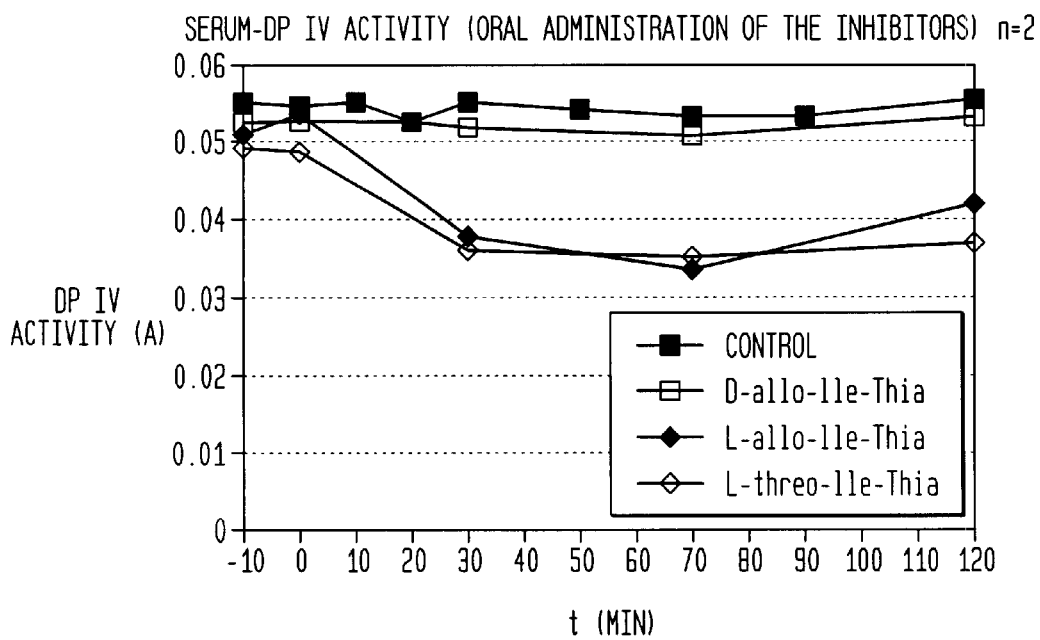
FIG. 3 depicts a graphic representation of serum DP VI activity after oral administration of various H-Ile-Thia stereoisomers (5 $\mu$M/300 g rat). Enazyme activity influenced only by L-Allo-Ile-Thia and L-threo-Ile-Thia.
Figure 4:
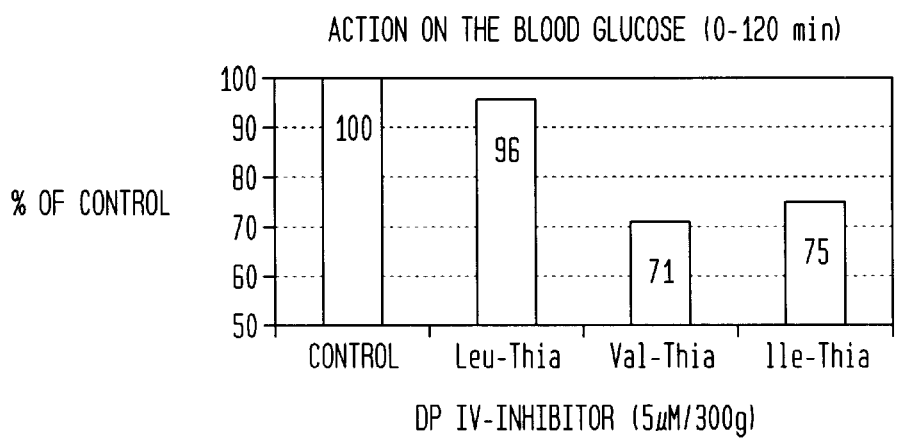
FIG. 4 depicts action of various aminoacyl-thiazolidides on the glucose tolerance of rats (oral glucose tolerance test with 2 g/300 g Wistar rat at time point, administration of DP IV inhibitors 10 minutes prior to oral glucose stimulation).

On administration, preferably oral administration, of these effectors to a mammalian organism, the endogenous (or additionally exogenously administered) insulinotropic peptides $GIP_{1-42}$ and $GLP-1_{7-36}$ (or alternatively $GLP-1_{7-37}$ or analogues thereof) are broken down to a reduced extent by DP IV or DP IV-like enzymes and therefore the decrease in the concentration of those peptide hormones or their analogues is reduced or delayed. The invention is therefore based on the finding that a reduction in the DP IV or DP IV-like enzymatic activity acting in the blood circulation has an effect on the blood sugar level. It has been found that 1. the reduction in DP IV or DP IV-analogous activity leads to an increase in the relative stability of the glucose-stimulated or externally introduced incretins (or analogues thereof), that is to say by administration of effectors of DP IV or DP IV-analogous proteins it is possible to control the breakdown of incretin in the blood;
2. the increase in the biological breakdown stability of the incretins (or their analogues) results in a change in the action of endogenous insulin;
3. the increase in the stability of the incretins brought about by the reduction in DP IV or DP IV-analogous enzymatic activity in the blood results in a subsequent change in the glucose-induced insulin action and therefore in a modulation of the blood glucose level that is controllable by means of DP IV-effectors.

Especially suitable for that purpose according to the invention are dipeptide compounds in which the amino acid is selected from a natural amino acid, such as, for example, leucine, valine, glutamine, proline, isoleucine, asparagine and aspartic acid.

The administration, where possible oral administration, of the high-affinity, low molecular weight enzyme inhibitors according to the invention is a more economical alternative e.g. to invasive surgical techniques in the treatment of pathological symptoms. Through a chemical design of stability, transport and clearance properties, their mode of action can be modified and matched to individual characteristics.

As mentioned above, it may be necessary, for example in the case of the long-term treatment of diabetes mellitus, to provide effectors having a defined activity with which it is possible to meet the individual needs of patients and to treat their symptoms. The dipeptide compounds according to the invention therefore exhibit at a concentration (of dipeptide compounds) of 10 $\mu$M, especially under the conditions indicated in Table 1, a reduction in the activity of dipeptidyl peptidase IV or DP IV-analogous enzyme activities of at least 10 %, especially of at least 40 %. Frequently a reduction in activity of at least 60 % or at least 70 % is also required. Preferred effectors may also exhibit a reduction in activity of a maximum of 20 % or 30 %. Furthermore, the transport properties of the present compounds, especially by the peptide transporter Pep T1, are significantly improved.

Especially preferred dipeptide compounds are L-allo-isoleucyl thiazolidide and salts thereof. Those compounds surprisingly exhibit an approximately five-fold improvement in transport by the peptide transporter Pep T1 in comparison with L-threo-isoleucyl thiazolidide, while having approximately the same degree of action with respect to glucose modulation.

Further illustrative compounds are given in Table 1.

The salts of the dipeptide compounds according to the invention may be, for example, organic salts such as acetates, succinates, tartrates or fumarates, or inorganic acid radicals such as phosphates or sulphates. Special preference is given to the fumarates, which have an excellent action combined with a surprisingly high degree of stability towards hydrolysis and are considerably less soluble than the hydrochlorides. Those properties are also advantageous from the galenical standpoint.

Also preferred are L-threo-isoleucyl pyrrolidide and salts thereof, especially the fumaric salts, and L-allo-isoleucyl pyrrolidide and salts thereof, especially the fumaric salts.

The salts of the dipeptide compounds can be present in a molar ratio of dipeptide (-analogous) component to salt component of 1:1 or 2:1. Such a salt is, for example, $(Ile-Thia)_2$ fumaric acid.

Especially preferred salts are the fumaric salts of L-threo-isoleucyl thiazolidide and L-allo-isoleucyl thiazolidide.

The invention accordingly relates to effectors of dipeptidyl peptidase IV (DP IV) or DP IV-analogous enzyme activity and their use in lowering the blood sugar level in the serum of a mammalian organism below the glucose concentration that is characteristic of hyperglycaemia. The invention relates especially to the use of the effectors of DP IV or DP IV-analogous enzyme activity according to the invention in preventing or alleviating pathological metabolic anomalies in mammalian organisms, such as, for example, impaired glucose tolerance, glycosuria, hyperlipidaemia, metabolic acidoses, diabetes mellitus, diabetic neuropathy and nephropathy and also sequelae or diabetes mellitus in mammals. In a further embodiment, the invention relates to a method of lowering the blood sugar level in the serum of a mammalian organism below the glucose concentration that is characteristic of hyperglycaemia, characterised in that a therapeutically effective amount of at least one effector of DP IV or DP IV-analogous enzyme activity according to the invention is administered to a mammalian organism.

In an alternative illustrative embodiment, the invention relates to pharmaceutical compositions, that is to say medicaments, that comprise at least one compounds according to the invention or a salt thereof, optionally in combination with one or more pharmaceutically acceptable carriers and/or solvents.

The pharmaceutical compositions may be, for example, in the form of parenteral or enteral formulations and may contain appropriate carriers or they may be in the form of oral formulations that may contain appropriate carriers suitable for oral administration. They are preferably in the form of oral formulations.

In addition, the pharmaceutical compositions may contain one or more active ingredients having a hypoglycaemic action, which may be active ingredients known by those skilled in the art.

The effectors of DP IV or DP IV-analogous enzyme activity according to the invention can be used for lowering the blood sugar level in the serum of a mammalian organism below the glucose concentration that is characteristic of hyperglycaemia or for the production of a corresponding medicament.

The effectors of DP IV or DP IV-analogous enzymes administered according to the invention can be used in pharmaceutically acceptable formulations or formulation complexes as inhibitors, substrates, pseudosubstrates, inhibitors of DP IV expression, binding proteins or antibodies of those enzyme proteins or combinations of those different substances that reduce the DP IV or DP IV-analogous protein concentration in the mammalian organism. Effectors according to the invention are, for example, DP IV-inhibitors such as the dipeptide derivatives or dipeptide mimetics L-allo-isoleucyl thiazolidide and the effectors indicated in Table 1 and fumaric salts thereof. The effectors according to the invention enable the treatment of patients and diseases to be adjusted individually, it being possible especially to avoid intolerances, allergies and side effects occurring in individual cases.

The compounds also exhibit different effectiveness behaviours over time. As a result, the physician carrying out the treatment has the opportunity to respond in various ways according to the individual situation of a patient: he is able, on the one hand, to set accurately the speed of onset of the action and, on the other hand, the duration of action and especially the strength of action.

The method according to the invention represents a new kind of procedure for lowering raised blood glucose concentrations in the serum of mammals. It is simple, capable of commercial exploitation and suitable for use in therapy, especially of diseases that are based on above-average blood glucose values, in mammals and more especially in human medicine.

The effectors are administered, for example, in the form of pharmaceutical preparations that comprise the active ingredient in combination with customary carrier materials known in the prior art. For example, they will be administered parenterally (e.g. i. v., in physiological saline) or enterally (e.g. orally, formulated with customary carrier materials, such as, for example, glucose).

Depending upon their endogenous stability and their bioavailability, the effectors will need to be administered one or more times per day in order to achieve the desired normalisation of the blood glucose values. For example, such a dosage range in human beings may lie in the range of from 0.01 mg to 30.0 mg per day, preferably in the range of from 0.01 to 10 mg of effector substance per kilogram of body weight.

It has been found that as a direct result of the administration of effectors of dipeptidyl peptidase IV or DP IV-analogous enzyme activities in the blood of a mammal, by virtue of the associated temporary reduction in the activity thereof, the endogenous (or additionally exogenously administered) insulinotropic peptides gastric inhibitory polypeptide 1-42 ($GIP_{1-42}$) and glucagon-like peptide amide-1 7-36 ($GLP-1_{7-36}$) (or alternatively $GLP-1_{7-37}$) or analogues thereof) are broken down to a reduced extent by DP IV and DP IV-like enzymes and thus the decrease in the concentration of those peptide hormones or their analogues is reduced or delayed. The increase in the stability of the (endogenously present or exogenously introduced) incretins or their analogues brought about by the action of DP IV-effectors, with the result that the former are available in increased amounts for insulinotropic stimulation of the incretin receptors of the Langerhan's cells in the pancreas, alters inter alia the effectiveness of the body's own insulin, which results in a stimulation of the carbohydrate metabolism of the treated organism.

As a result, the blood sugar level in the serum of the organism being treated falls below the glucose concentration that is characteristic of hyperglycaemia, thus making it possible to prevent or alleviate metabolic anomalies such as impaired glucose tolerance, glycosuria, hyperlipidaemia and possible severe metabolic acidoses and diabetes mellitus, which are clinical syndromes resulting from raised glucose concentrations in the blood over a prolonged period.

Among the number of orally effective anti-diabetics known from the prior art, such an effective low molecular weight substance class has been unknown hitherto (with the exception of the biguanide metformin: molecular weight 130). The molecular weights of the aminoacyl thiazolidides vary between 146 (glycyl thiazolidide), 203 (isoleucyl thiazolidide) and 275 (tryptophanyl thiazolidide). In comparison, the molecular weights of the sulphonylureas (glibenclamide: 494), the saccharides (acarbose: 630) and the thiazolidinediones (pioglitazon: 586) vary in the range around 500 to 700 Da. In the body, aminoacyl thiazolidides are hydrolysed by aminopeptidases and by acidic hydrolysis to form endogenous substances, such as amino acids and cysteamine, so that the use of the compounds according to the invention as orally available anti-diabetics constitutes an enrichment of pharmacy.

In rats and mice, experimentally induced hyperglycaemia can be treated to a better than average extent by oral administration of the compounds used according to the invention as shown in Tables 2 and 3. The administration of 500 to 1000 times the effective dose did not result in any demonstrable pathological change during three-week toxicological experiments on rats and mice.

The advantageous action of compounds according to the invention on DP IV is shown by way of example in Table 1:

TABLE 1

Action of various effectors on the dipeptidyl-peptidase-IV-catalysed hydrolysis of 0.4 mM of the substrate H-Gly-Pro-pNA at 30° C., pH 7.6 and an ionic strength of 0.125

| Effector | Effector affinity to DP IV: $K_i$ [nM] | % Residual activity of DP IV in the presence of 10 μM effector |
|---|---|---|
| metformin | >>1,000,000 | 100 |
| glibenclamide | >>1,000,000 | 100 |
| acarbose | 1,000,000 | 100 |
| H-Asn-pyrrolidide | 12,000 | 83.1 |
| H-Asn-thiazolidide | 3,500 | 47.2 |
| H-Asp-pyrrolidide | 14,000 | 81.6 |
| H-Asp-thiazolidide | 2,900 | 45.6 |
| H-Asp(NHOH)-pyrrolidide | 13,000 | 88.2 |
| H-Asp(NHOH)-thiazolidide | 8,800 | 54.5 |
| H-Glu-pyrrolidide | 2,200 | 38.5 |
| H-Glu-thiazolidide | 610 | 25.0 |
| H-Glu(NHOH)-pyrrolidide | 2,800 | 44.9 |
| H-Glu(NHOH)-thiazolidide | 1,700 | 36.5 |
| H-His-pyrrolidide | 3,500 | 49.7 |
| H-His-thiazolidide | 1,800 | 35.2 |
| H-Pro-pyrrolidide | 4,100 | 50.2 |
| H-Pro-thiazolidide | 1,200 | 27.2 |
| H-Ile-azididide | 3,100 | 43.8 |
| H-Ile-pyrrolidide | 210 | 12.3 |
| H-L-allo-Ile-thiazolidide | 190 | 10.0 |
| H-Val-pyrrolidide | 480 | 23.3 |
| H-Val-thiazolidide | 270 | 13.6 |

It is known that aminoacyl pyrrolidides and aminoacyl thiazolidides can be broken down by the enzymes proline aminopeptidase and prolidase present in the mucosa cells of the small intestine, in serum and in liver cells and that the thiazolidine ring has a tendency to open in the presence of acids (for example in the stomach) with the formation of the corresponding cysteamine derivative. It was therefore surprising to find that the active ingredients have a dose-dependent effectiveness after peroral administration. The dose-dependency of the action of L-allo-Ile- thiazolidide on the serum-DP IV activity after oral administration of L-allo-isoleucyl thiazolidide to healthy Wistar rats is documented in the following Table:

TABLE 2

Residual activity of DP IV in serum towards 0.4 mM of the substrate H-Gly-Pro-pNA at 30° C., ph 7.6 and an ionic strength of 0.125, after oral administration and in dependence upon the dose of L-allo-isoleucyl thiazolidide, determined 30 min after administration of the inhibitor

| Dose per experimental animal | Residual activity of DP IV in % |
|---|---|
| 0 mg | 100 |
| 2.5 mg | 52 |
| 5.0 mg | 40 |
| 10 mg | 28 |
| 20 mg | 29 |

Extremely surprising and desirable is the glucose-reducing action of the active ingredient L-allo- isoleucyl thiazolidide according to the invention achieved in the diabetic animal model after oral administration with synchronous oral glucose stimulation as shown in Table 3.

In order to intensify the blood-sugar-reducing action of various anti-diabetics, use is frequently made of combinations of different orally effective anti-diabetics. Since the anti-hyperglycaemic action of the effectors according to the invention is exhibited independently of other known oral anti-diabetics, the active ingredients according to the invention are analogously suitable for use in combination therapies, in a suitable galenical form, for achieving the desired normoglycaemic effect.

Accordingly, the compounds used according to the invention can be made in a manner known by those skilled in the art into the customary formulations, such as, for example, tablets, capsules, dragees, pills, suppositories, granules, aerosols, syrups, liquid, solid and cream-type emulsions and suspensions and solutions using inert, non-toxic, pharmaceutically acceptable carriers and additives or solvents. In such formulations the therapeutically effective compounds are in each case preferably present in a concentration of approximately from 0.1 to 80% by weight, preferably from 1 to 50% by weight, of the total mixture, that is to say in amounts sufficient to achieve a dosage within the indicated range.

TABLE 3

Reduction in the circulating blood glucose within a period of 60 min after oral administration of 20 $\mu$M of L-allo-Ile thiazolidide to rats of various animal models with a synchronous glucose tolerance test (data in % based on normoglycaemic values).

| Animal model | Glucose concentration in % control | Glucose concentration in % L-allo-Ile-thiazolidide-treated |
|---|---|---|
| Wistar rat, normal | 100 | 82 |
| Wistar rat (diabetes 2b-model, obese) | 100 | 73 |

The good absorption of the compounds used according to the invention by mucosae of the gastro-intestinal tract enables a large number of galenical preparations to be used:

The substances can be administered as medicaments in the form of dragees, capsules, bitable capsules, tablets, drops and syrup, as well as in the form of pessaries and nasal sprays.

The formulations are produced, for example, by extending the active ingredient with solvents and/or carriers, optionally using emulsifiers and/or dispersing agents, and optionally, for example where water is used as diluent, organic solvents may be used as auxiliary solvents.

The following auxiliaries may be mentioned by way of example: water, non-toxic organic solvents, such as paraffins (e.g. mineral oil fractions), vegetable oils (e.g. rapeseed oil, groundnut oil, sesame oil), alcohols (e.g. ethyl alcohol, glycerol), glycols (e.g. propylene glycol, polyethylene glycol); solid carriers, such as, for example, ground natural minerals (e.g. highly dispersed silicic acid, silicates), sugars (e.g. unrefined sugar, lactose and dextrose); emulsifiers, such as non-ionic and anionic emulsifiers (e.g. polyoxyethylene fatty acid esters, polyoxyethylene fatty alcohol ethers, alkylsulphonates and arylsulphonates), dispersing agents (e.g. lignin, spent sulphite liquors, methylcellulose, starch and polyvinylpyrrolidone) and glidants (e.g. magnesium stearate, talcum, stearic acid and sodium lauryl sulphate) and optionally flavourings.

Administration is effected in customary manner, preferably enterally or parenterally, especially orally. In the case of enteral administration, in addition to containing the mentioned carriers, tablets may also comprise other additives, such as sodium citrate, calcium carbonate and calcium phosphate, together with various supplementary ingredients, such as starch, especially potato starch, gelatin and the like. It is also possible to use glidants, such as magnesium stearate, sodium lauryl sulphate and talcum, for tableting purposes. In the case of aqueous suspensions and/or elixirs intended for oral uses it is also possible for various taste correctors or colorings to be added to the active ingredients in addition to the auxiliaries mentioned above.

For parenteral administration it is possible to use solutions of the active ingredients using suitable liquid carrier materials. In the case of intravenous administration it has generally proved advantageous to administer amounts of approximately from 0.01 to 2.0 mg/kg, preferably approximately from 0.01 to 1.0 mg/kg, body weight per day in order to achieve effective results, and in the case of enteral administration the dosage is approximately from 0.01 to 2 mg/kg, preferably approximately from 0.01 to 1 mg/kg, body weight per day.

Nevertheless in some cases it may be necessary to depart from the amounts indicated, depending upon the body weight of the experimental animal or patient or the nature of the administration route, and also on the basis of the species of animal and its individual response to the medicament or the intervals at which the administration is made. In some cases, for example, it may be sufficient to use less than the above-mentioned minimum amount, whereas in other cases it will be necessary to exceed the above-mentioned upper limit. Where relatively large amounts are administered it may be advisable to divide the amount into several individual doses over the day. For use in human medicine the same range of dosage is provided, the comments made above also applying accordingly.

EXAMPLES OF PHARMACEUTICAL FORMULATIONS

1. Capsules having 100 mg of L-allo-isoleucyl thiazolidide per capsule:

For about 10,000 capsules, a solution of the following composition is prepared:

| | |
|---|---|
| L-allo-isoleucyl thiazolidide hydrochloride | 1.0 kg |
| glycerol | 0.5 kg |
| polyethylene glycol | 3.0 kg |
| water | 0.5 kg |
| | 5.0 kg |

The solution is introduced into soft gelatin capsules in a manner known by those skilled in the art. The capsules are suitable for chewing or swallowing.

2. Tablets/coated tablets or dragees having 100 mg of L-allo-isoleucyl thiazolidide:

The following amounts relate to the production of 100,000 tablets: L-allo-isoleucyl thiazolidide hydrochloride,

| | |
|---|---|
| finely ground | 10.0 kg |
| glucose | 4.35 kg |
| lactose | 4.35 kg |
| starch | 4.50 kg |
| cellulose, finely ground | 4.50 kg |

The above constituents are mixed together and then combined with a solution, prepared from

| | |
|---|---|
| polyvinylpyrrolidone | 2.0 kg |
| polysorbate | 0.1 kg |
| and water | about 5.0 kg | and granulated in a manner known by those skilled in the art by grating the moist mass and, after the addition of 0.2 kg of magnesium stearate, drying. The finished tablet mixture of 30.0 kg is processed to form domed tablets each weighing 300 mg. The tablets can be coated or sugar-coated in a manner known by those skilled in the art.

The technical data of illustrative compounds are shown in Table 4.

TABLE 4

Tests on Ile-Thia*fumarate (isomer) and other salts (FIG. 1)

| Substance | $K^i$ | Mp(° C.) | CE(min) | MS | $[\alpha]H_2O$ |
|---|---|---|---|---|---|
| L-threo-IT*F | $8*10^{-8}$ | $150^{DSC}$ | 160 | 203 | −10.7 (405 nm) |
| D-threo-IT*F | no inhibition | 147 | 158 | 203 | not determined |
| L-allo-IT*F | $2*10^{-7}$ | 145–6 | 154 | 203 | −4.58 (380 nm) |
| D-allo-IT*F | no inhibition | 144–6 | 150 | 203 | 4.5 (380 nm) |

IT*F = isoleucyl thiazolidide fumarate
The NMP and HPLC data confirm the identity of the substances in question.

Measurement conditions for the $K_1$ determination of the substances
Enzyme: DP $Iv_{porcine\ kidney}$, 0.75 mg/ml, 18 U/ml (GPpNA) in 25mM Tris pH 7.6, 30% ammonium sulphate, 0.5 mM EDTA, 05 mM DTE Stock solution: 1:250 diluted in measuring buffer
Buffer: 40mM HEPES pH 7.6,I=0.125 (KC1)
Substrate: GPPNA*HC1Stock solution: 2.1 mM
Measuring
apparatus: Perkin-Elmer Bio Assay Reader, HTS 7000 Plus, T=30° C. λ=405 nm
Measurement
batch: 100 μl buffer 100 μl substrate (3 different concentrations 0.8 mM–0.2 mM) 50 μl water/inhibitor (7 different concentrations 2.1 μM–32.8 nM) 10 μl enzyme
Buffer, water/inhibitor and enzyme were preheated to 30° C. and the reaction was started by the addition of substrate which was likewise preheated. Determinations were carried out four times. The measuring time was 10 minutes.
Melting point determination Melting points were determined on a Kofler heating platform microscope from Leica Aktiengesellschaft, the values are not corrected, or on a DSC apparatus (Heumann-Pharma).

Optical rotation
The rotation values were recorded at different wavelengths on a "Polarimeter 341" or higher, from the Perkin-Elmer company.

Measurement conditions for the mass spectroscopy
The mass spectra were recorded by means of electrospray ionisation (ESI) on an "API 165" or "API 365" from the PE Sciex Company. The operation is carried out using an appropriate concentration of c=10 μg/ml, the substance is taken up in MeOH/H₂O 50:50, 0.1% HCO₂H, the infusion is effected using a spray pump (20 μl/min). The measurements were made in positive mode $[M+H]^+$, the ESI voltage is U=5600 V.

The salts have the following data which is shown in Table 5.:

TABLE 5

| IT*salt | $K_i$ | M (gmol$^{-1}$) | Mp (° C.) |
|---|---|---|---|
| succinate | 5.1 e-8 | 522.73 | 116 |
| tartrate | 8.3 e-8 | 352.41 | 122 |
| fumarate | 8.3 e-8 | 520.71 | 156 |
| hydrochloride | 7.2 e-8 | 238.77 | 169 |
| phosphate | 1.3 e-7 | 300.32 | 105 |

Testing the solubility of salts of Ile-Thia
Ile-Thia*fum
  Amount weighed in 10.55 mg
  corresponds to 0.02 mmol (520.72 g/mol)
  Addition of 100 μl H₂O$_{dist}$.
  100 μl no solution, visually: no surface-wetting
  from 200 μl successive beginning of solubility
  at 400 μl complete dissolution is observed
  2.63%
It is therefore established that this salt is scarcely wettable and does not decompose.
Ile-Thia*succ
  Amount weighed in 16.6 mg
  corresponds to 0.031 mmol (522.73 g/mol)
  Addition of 16 μl H₂O$_{dist}$.
  16 μl no solution, visually: "sucking-up" of the moisture
    from 66 μl −1.5 ml no complete dissolution of the substance is observed
Ile-Thia*tartrate
  Amount weighed in 17.3 mg
  corresponds to 0.049 mmol (352.41 g/mol)
  Addition of 100 μl H₂O$_{dist}$.
  100 μl complete dissolution
  17.3%
Ile-Thia*phos
  Amount weighed in 15.5 mg
  corresponds to 0.051 mmol (300.32 g/mol)
  Addition of 100 μl H₂O$_{dist}$.
  100 μl slight dissolution is observed
  successive addition of 100 μl H₂O
  at 400 μl complete dissolution
  3.87%
Ile-Thia*HC1
  Amount weighed in 16.1 mg
  corresponds to 0.067 mmol 238.77 (g/mol)
  Addition of 100 μl H₂O$_{dist}$.
  at 100 μl complete dissolution
  16.1%

General synthesis of Ile-Thia*salt

The Boc-protected amino acid Boc-Ile-OH is placed in ethyl acetate and the batch is cooled to about −5° C. N-Methylmorpholine is added dropwise, pivalic acid chloride (on a laboratory scale) or neohexanoyl chloride (on a pilot-plant scale) is added dropwise at constant temperature. The reaction is stirred for a few minutes for activation. N-Methylmorpholine (laboratory scale) an thiazolidine hydrochloride (laboratory scale) are added dropwise in succession, thiazolidine (pilot-plant scale) is added. Working-up in the laboratory is effected in conventional manner using salt solutions, on a pilot-plant scale the batch is purified with NaOH and $CH_3COOH$ solutions. The removal of the Boc protecting group is carried out using HCl/dioxane (laboratory scale) or $H_2SO_4$ (pilot-plant scale). In the laboratory the hydrochloride is crystallised from EtOH/ether. On a pilot-plant scale the free amine is prepared by the addition of $NaOH/NH_3$. Fumaric acid is dissolved in hot ethanol, the free amine is added dropwise, and (Ile-Thia)$_2$ fumarate (M=520.71 gmol$^{-1}$) precipitates.

The analysis of isomers and enantiomers is carried out by electrophoresis.

What is claimed is:

1. A pharmaceutical composition for the treatment of metabolic disorders comprising: a salt form of a dipeptide compound formed from an amino acid and a thiazolidine or pyrrolidine group, in combination with pharmaceutically acceptable carriers or solvents, wherein said salts are selected from the group consisting of acetates, succinates, tartrates, fumarates, phosphates and sulphates.

2. The pharmaceutical composition according to claim 1, wherein said amino acid is selected from a natural amino acid.

3. The pharmaceutical composition according to claim 1 wherein said dipeptide compound at a concentration of 10 $\mu$M reduces the activity of dipeptidyl peptidase IV (DP IV) or DP-IV-analogous enzyme in the amount of at least 10%.

4. The pharmaceutical composition according to claim 1 wherein said dipeptide compound reduces the activity of dipeptidyl peptidase IV (DP IV) or DP-IV-analogous enzyme in the amount of at least 40%.

5. The pharmaceutical composition according to claim 1, wherein said amino acid is selected from leucine, valine, glutamine, proline, isoleucine, asparagine and aspartic acid.

6. The pharmaceutical composition according to claim 1, wherein said dipeptide compound is selected from a group consisting of: L-threo-isoleucyl pyrrolidine, L-allo-isoleucyl thiazolidine, L-allo-isoleucylpyrrolidine.

7. The pharmaceutical composition according to claim 1, wherein said salts are present in a molar ratio of dipeptide compound to salt of 1:1 or 2:1.

8. The pharmaceutical composition according to claim 1, wherein said salts are fumaric salts.

9. The pharmaceutical composition according to claim 8, wherein said fumaric salts of dipeptide compounds are selected from the group consisting of L-threo-isoleucyl thiazolidine and L-allo-isoleucyl thiazolidine.

10. A pharmaceutical composition comprising dipeptide compounds and analogs thereof that are selected from the salts of the group consisting of L-threo-isoleucyl pyrroldine, L-allo-isoleucyl thiazolidine, L-allo-isoleucyl pyrrolidine in combination with pharmaceutically acceptable carriers or solvents, wherein said salts are selected from the group consisting of acetates, succinates, tartrates, fumarates, phosphates and sulphates.

11. The pharmaceutical composition according to claim 10, wherein said carrier is suitable for parenteral or enteral formulations.

12. The pharmaceutical composition according to claim 10, wherein said carrier is suitable for an oral administration formulation.

13. The pharmaceutical composition according to claim 10 wherein said composition additionally comprises an active ingredient having hypoglycaemic action selected from the group consisting of biguanide metformin, sulphonylureas, saccharides and thiazolidinediones.

14. The pharmaceutical composition according to claim 1 wherein said metabolic disorder is selected from the group consisting of impaired glucose tolerance, glycosuria, hyperlipidaemia, metabolic acidosis, diabetic neuropathy, nephropathy and diabetes mellitus.

* * * * *